United States Patent
Baxter et al.

(10) Patent No.: US 6,562,960 B1
(45) Date of Patent: May 13, 2003

(54) OLIGONUCLEOTIDE ANALOGUES

(75) Inventors: Anthony David Baxter, Abingdon (GB); Stephen Paul Collingwood, Crawley (GB); Mark Edward Douglas, Macclesfield (GB); Roger John Taylor, Wouthwater (GB)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/142,212

(22) PCT Filed: Feb. 24, 1997

(86) PCT No.: PCT/GB97/00499

§ 371 (c)(1),
(2), (4) Date: Oct. 9, 1998

(87) PCT Pub. No.: WO97/32887

PCT Pub. Date: Sep. 12, 1997

(30) Foreign Application Priority Data

Mar. 5, 1996 (GB) ............................................. 9604669

(51) Int. Cl.$^7$ ........................... C07H 21/00; C12P 19/34
(52) U.S. Cl. .................... 536/25.3; 536/23.1; 536/24.5; 435/91.1
(58) Field of Search .............................. 536/24.5, 25.1, 536/25.34, 23.1, 25.3, 25.33; 525/54.11; 435/6, 91.1

(56) References Cited

U.S. PATENT DOCUMENTS

| | | | | |
|---|---|---|---|---|
| 4,469,863 A | * | 9/1984 | Miller et al. | 536/24.5 |
| 4,507,433 A | * | 3/1985 | Miller et al. | 536/24.5 |
| 5,610,289 A | * | 3/1997 | Cook et al. | 536/25.34 |
| 6,033,909 A | * | 3/2000 | Uhlmann et al. | |

FOREIGN PATENT DOCUMENTS

| | | |
|---|---|---|
| EP | 0 266 099 | 5/1988 |
| EP | 0 307 362 | 3/1989 |
| WO | WO 87/07300 | 12/1987 |
| WO | WO 89/08146 | 9/1989 |
| WO | WO 91/06556 | 5/1991 |
| WO | WO 92/20822 | 11/1992 |
| WO | WO 92/20823 | 11/1992 |
| WO | WO 95/02069 | 1/1995 |
| WO | WO 95/26972 | 10/1995 |
| WO | WO95/32987 | * 12/1995 |
| WO | WO 96/08503 | 3/1996 |

OTHER PUBLICATIONS

Andrea D. Branch, A good antisense molecule is hard to find, TIBS, 47–48, Feb. 1998.*
Stanley Crooke, Antisense Research and Applications, Chapter 1, Basic Principles of Antisense Therapeutics, Springer–Verlag Press, Berlin, Heidelberg, New York, p. 3, Jul. 1998.*
Andrus, Alex et al., Nucleic Acids Research, Symposium Series No. 20, pp. 121–122 (1988).
Beaucage, S. L. et al., Tetrahedron, vol. 49, No. 10, The Functionalization of Oligonucleotides Via Phosphoramidite Derivatives, pp. 1925–1963 (1993).
Brill, W. K–D, Tetrahedron Letters, vol. 36, No. 5, Thio–alkylation of Nucleoside–H–phosphonates and its Application to Solid Synthesis of Oligonucleotides, pp. 703–706 (1995).
Heinemann, U. et al., Nucleic Acids Research, vol. 19, No. 3, "Effect of a single 3'–methylene phosphonate linkage on the conformation of an A–DNA octomer double helix", pp. 427–433 (1991).
Jones, G.H. et al., Journal of the American Chemical Society, vol. 92(18), Communications to the Editor; "Synthesis of Isosteric Phosphonate Analogs of some Biologically Important Phosphodiesters", pp. 5510–5511 (1970).
Mazur, A. et al., Tetrahedron, vol. 40, No. 20. Isosteres of Natural Phosphates. 11. "Synthesis of a Phosphonic Acid an Analogue of an Oligonucleotide.", pp. 3949–3956 (1984).
Morr, M. et al., GBF Monographs—Chemical Synthesis in Molecular Biology, vol. 8, "Building Blocks for the Chemical Synthesis of DNA Containing C(3')–C$_2$–P Bonds", pp. 107–113 (1987).
Petrakis, K.S. et al., J. of Am. Chem. Soc., vol. 109, pp. 2831–2833 (1987).
Xu, Y. et al., Tetrahedron Letters, vol. 30, No. 8, "An Efficient Synthesis of Chiral, Nonracemic Isopropyl Alkenylmethylphosphinates Via Palladium Route", pp. 949–952 (1989).
Zain, R et al., J. Org. Chem., vol. 60, pp. 8241–8244 (1995).

* cited by examiner

Primary Examiner—Sean McGarry
Assistant Examiner—Janet L. Epps-Ford
(74) Attorney, Agent, or Firm—Woodcock Washburn LLP

(57) ABSTRACT

An oligonucleotide analogue having 10 to 200 natural and/or synthetic nucleoside units, linked by internucleoside linkages, at least one of the internucleoside linkages being of formula

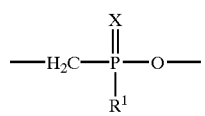

where the indicated methylene group is attached to a 3' carbon atom of a nucleoside, the indicated oxygen atom is attached to a 5'-carbon atom of an adjacent nucleside, $R^1$ is hydrogen, hydroxy, O—, thiol, S—, —NH$_2$ or a group of formula $R_{1a}$, —OR$_{1a}$, —SR$_{1a}$, —NHR$_{1b}$, or —NR$_{1b}$R$_{1c}$ wherein $R_{1a}$ is an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group; and $R_{1b}$ and $R_{1c}$ are each independently an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group or $R_{1b}$ and $R_{1c}$ together with the nitrogen atom to which they are attached denote a five- or six-membered heterocyclic ring, and X is oxygen or sulfur.

45 Claims, No Drawings

SEQUENCE LISTING

```
<160> NUMBER OF SEQ ID NOS:  13

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 1
tcccgcctgt gacatgcatt                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:  Synthetic
      Oligonucleotide

<400> SEQUENCE: 2
gttctcgctg gtgagtttca                                                   20

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (4)
<223> OTHER INFORMATION: Modified internucleoside linkage

<400> SEQUENCE: 3
tttttctctc tctct                                                        15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (4)
<223> OTHER INFORMATION: Modified internucleoside linkage
<221> NAME/KEY: misc_feature
<222> LOCATION: (5)
<223> OTHER INFORMATION: A thymidine residue having an alpha-methoxy
      group present at the 2'-position rather than a hydrogen
      atom
```

-continued

<400> SEQUENCE: 4
tttttctctc tctct                                                            15

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (5)
<223> OTHER INFORMATION: Modified internucleoside linkage

<400> SEQUENCE: 5
tttttctctc tctct                                                            15

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (1)..(5)
<223> OTHER INFORMATION: Modified internucleoside linkage

<400> SEQUENCE: 6
tttttctctc tctct                                                            15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (11)
<223> OTHER INFORMATION: Modified internucleoside linkage
<221> NAME/KEY: misc_feature
<222> LOCATION: (13)
<223> OTHER INFORMATION: Modified internucleoside linkage

<400> SEQUENCE: 7
cgactatgca ttttc                                                            15

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (4)..(13)
<223> OTHER INFORMATION: Modified internucleoside linkage

<400> SEQUENCE: 8
gcgttttttt tttgcg                                                           16

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic

```
                Oligonucleotide
<221> NAME/KEY: misc_feature
<222> LOCATION: (5)..(6)
<223> OTHER INFORMATION: Modified internucleoside linkage

<400> SEQUENCE: 9
tttttctctc tctct                                                    15

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (16)..(18)
<223> OTHER INFORMATION: Modified internucleoside linkage

<400> SEQUENCE: 10
tttttttttt ttttttttt                                                19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (1)..(5)
<223> OTHER INFORMATION: Modified internucloside linkage
<221> NAME/KEY: misc_feature
<222> LOCATION: (14)..(19)
<223> OTHER INFORMATION: Modified internucleoside linkage

<400> SEQUENCE: 11
ttctcgcccg ctcctcctcc                                               20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (1)..(5)
<223> OTHER INFORMATION: Modified internucleoside linkage
<221> NAME/KEY: misc_feature
<222> LOCATION: (15)..(18)
<223> OTHER INFORMATION: Modified internucleoside linkage

<400> SEQUENCE: 12
ttctcgctgg tgagtttca                                                19

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      Oligonucleotide
<221> NAME/KEY: misc_feature
<222> LOCATION: (4)
<223> OTHER INFORMATION: A nucleoside unit derived from Compound M

<400> SEQUENCE: 13
tttttctctc tctct                                                    15
```

OLIGONUCLEOTIDE ANALOGUES

This invention relates to oligonucleotide analogues, their preparation and their use.

In accordance with the invention, oligonucleotide analogues can be prepared which have good hybridisation properties to single- and double-stranded nucleic acids, RNase H-activating properties, good hydrolytic stability and good stability towards cleavage by nucleases, facilitating their use as inhibitors of gene expression, for example by antisense interaction, and as pharmaceuticals in the treatment of diseases such as cancer and viruses such as influenza, herpes and HIV.

Accordingly, the present invention provides an oligonucleotide analogue having 10 to 200 natural and/or synthetic nucleoside units linked by internucleoside linkages, at least one of the internucleoside linkages being of formula

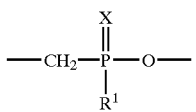

I where the indicated methylene group is attached to a 3' carbon atom of a nucleoside, the indicated oxygen atom is attached to a 5' carbon atom of an adjacent nucleoside, $R^1$ is hydrogen, hydroxy, $O^-$, thiol, $S^-$, $-NH_2$ or a group of formula $R^1_a$, $-OR^1_a$, $-SR^1_a$, $-NHR^1_b$ or $-NR^1_bR^1_c$ where $R^1_a$ is an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group and $R^1_b$ and $R^1_c$ are each independently an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group or $R^1_b$ and $R^1_c$ together with the nitrogen atom to which they are attached denote a five- or six-membered hetercyclic ring, and X is oxygen or sulphur.

The number of nucleoside units in the oligonucleotide analogue may vary, for example from 15 to 100, according to the nature of the nucleic acid sequence to which the oligonucleotide analogue is targeted. Preferably, the oligonucleotide analogue has 15 to 40, especially 15 to 25 nucleoside units. The oligonucleotide analogue may more preferably have 15 to 20 nucleoside units for certain targets, 20 to 25 nucleoside units for other targets, 18 to 25 nucleoside units for further targets and 18 to 22 nucleoside units for yet further targets.

In an oligonucleotide analogue of the invention, the number of internucleoside linkages of formula I may vary according to the properties desired. For example, for some purposes one internucleoside linkage of formula I may suffice, while for other purposes all the internucleoside linkages may be of formula I and may be the same or different. For most purposes, up to 75%, for example up to 50%, particularly up to 25%, of the internucleoside linkages may be of formula I.

In some embodiments of the invention, at least two consecutive internucleoside linkages, for example two, three, four, five or six consecutive internucleoside linkages, which may be the same or different, in the oligonucleotide analogue are of formula I. There may be such a sequence of consecutive internucleoside linkages at each end of the oligonucleotide analogue; more usually, there is one such sequence of consecutive internucleoside linkages of formula I between sequences of nucleosides having other internucleoside linkages. In other embodiments of the invention having two or more internucleoside linkages of formula I, internucleoside linkages of formula I may alternate with other internucleoside linkages, for example along the whole length of the oligonucleotide analogue or in a region at one or both ends of the oligonucleotide analogue, or in a region in the middle of the oligonucleotide analogue.

In embodiments of the invention where not all of the internucleoside linkages are of formula I, the remaining internucleoside linkages may be natural phosphodiester linkages or other synthetic substitutes therefor such as phosphorothioate, phosphorodithioate, alkylphosphonate $(-O-P(O)(R)O-)$, phosphoramidate, short chain alkyl, cycloalkyl, short chain heteroatomic, $-NHCOCH_2-$, $-CH_2NHCO-$, $-CONHCH_2-$, $-CH_2CONH-$, $-CH_2NHO-$, $-CH_2N(CH_3)O-$, $-CH_2ON(CH_3)-$, $-CH_2N(CH_3)N(CH_3)-$ or $-ON(CH_3) CH_2-$ linkages, or combinations of two or more such linkages. Preferably, the remaining internucleoside linkages are phosphodiester, phosphorothioate or phosphorodithioate linkages or a mixture of two or more of these three types, particularly phosphodiester, phosphorothioate or a mixture of phosphodiester and phosphorothioate linkages. In certain especially preferred embodiments the remaining internucleoside linkages are phosphorothioate linkages.

Preferably, not more than 50% of the internucleoside linkages are phosphorothioate linkages.

In certain embodiments of the invention, the oligonucleotide comprises a region having phosphodiester and/or phosphorothioate and/or phosphorodithioate internucleoside linkages between two regions having internucleoside linkages of formula I, or a mixture thereof with phosphorothioate or phosphodiester linkages, particularly a region having phosphorothioate linkages between two regions having internucleoside linkages of formula I or a mixture thereof with phosphorothioate or phosphodiester linkages.

In some especially preferred embodiments, the oligonucleotide analogue of the invention comprises a region of at least 6 nucleosides linked by phosphorothioate linkages between two regions having nucleosides linked only by internucleoside linkages of formula I.

In oligonucleotide analogues of the invention, the nucleoside units may be natural or synthetic nucleosides having a purine or pyrimidine base such as adenine, guanine, cytosine, thymine or uracil, or an analogue of these bases such as 2-aminoadenine, 6-hydroxypurine, 5-methylcytosine, 5-propynylcytosine, 5-fluorouracil, 5-propynyluracil or dihydrouracil, attached to the I' carbon atom of a furanose sugar. As is well understood by those skilled in the art, when the oligonucleotides are for use in antisense applications, the sequence of nucleosides is chosen to be complementary to a target RNA sequence. For example, the oligonucleotide analogue of the invention may be complementary to a region of mRNA for human c-raf kinase, in which case, a preferred sequence is 5'-TCC CGC CTG TGA CAT GCA TT-3' SEQ ID NO:1.
described as Seq. ID No. 8 in WO 95/32987 or the oligonucleotide analogue of the invention may be complementary to a region of mRNA for human PKC-α, in which case a preferred sequence is 5'-GTT CTC GCT GGT GAG TTT CA-3' SEQ ID NO:2
described as Seq. ID No. 2 in WO 95/02069.

In some oligonucleotide analogues of the invention, at least one nucleoside is modified at the 2' position thereof, for example to increase binding affinity for a given target and/or to increase nuclease resistance. All of the nucleosides may be so modified, or up to 80%, for example up to 70%, up to 60%, up to 50%, up to 40%, up to 30%, up to 20%, or up to 10%, of the nucleosides, may be so modified. Examples of 2' modifying atoms and groups, i.e. atoms or groups which may be attached to the 2' position of a nucleoside in place of a hydrogen atom or hydroxy group to effect a modification, include halogen atoms such as fluorine, chlorine and bromine atoms; $C_1$ to $C_{10}$ unsubstituted or substituted alkyl groups such as methyl, trifluoromethyl, ethyl, propyl, butyl, pentyl, hexyl, octyl or decyl; $C_6$ to $C_{10}$ aryl groups such as phenyl, tolyl or xylyl; $C_7$ to $C_{13}$ aralkyl groups such as benzyl; amino, $C_1$ to $C_{10}$ alkyl amino such as methylamino, ethylamino or octylamino; $C_1$ to $C_{10}$ alkylthio such as methylthio, ethylthio or octylthio; azide; nitrate; nitrite; cyanide; cyanate; methanesulphonate; $C_1$ to $C_{10}$ aminoalkylamino; a group of formula —$OR^2$ where $R^2$ is a $C_1$ to $C_{10}$ aliphatic group; substituted silyl; an RNA cleaving group; a cholesteryl group; a conjugate; a reporter group; an intercalator, a group for improving the pharmacokinetic properties of an oligonucleotide; and a group for improving the pharmacodynamic properties of an oligonucleotide.

Preferred modifying atoms and groups at the 2' position are halogen atoms, especially fluorine, and a group of formula —$OR^2$ where $R^2$ is a $C_1$ to $C_{10}$ aliphatic group, which may be an unsubstituted or substituted $C_1$ to $C_{10}$ alkyl group such as methyl, ethyl, isopropyl, butyl, hexyl, octyl, decyl, trifluoromethyl, ethoxyethyl, methoxyethyl, or butoxyethyl, or a $C_2$ to $C_6$ alkenyl group such as vinyl, allyl or methallyl. Particularly preferred modifying atoms and groups are fluorine and groups of formula —$OR^2$ where $R^2$ is an unsubstituted or substituted $C_1$ to $C_{10}$ alkyl group, preferably $C_1$ to $C_4$ alkyl, $C_1$ to $C_4$ alkoxy-substituted $C_1$ to $C_4$ alkyl or a group of formula —$(CH_2CH_2O)$—$_nR^3$ when $R^3$ is methyl or ethyl and n is 2 to 4. Especially preferred groups of formula —$OR^2$ are those where $R^2$ is methyl, ethyl, methoxyethyl, ethoxyethyl or a group of formula —$(CH_2CH_2O)$—$_3CH_3$.

When nucleosides modified at the 2' position are present, an oligonucleotide analogue of the invention may have, for example, at least two consecutive nucleosides modified at the 2' position and linked by phosphodiester internucleoside linkages and/or it may have an internucleoside linkage of formula I between a nucleoside unmodified at the 2' position and a 5' carbon atom of a nucleoside modified at the 2' position.

As is also well understood by those skilled in the art, the terminal nucleosides in the oligonucleotide analogue may have free 5' and 3' hydroxy groups respectively or may have either or both of these hydroxy groups replaced by a modifying group, for example a phosphate, thiol, alkylthio, thioalkyl, thiophosphate, aminoalkyl, acridinyl, cholesteryl or fluoresceinyl group.

In linkages of formula I, $R^1_a$, $R^1_b$ or $R^1_c$ as a substituted alkyl, alkenyl, cycloalkyl, aryl or aralkyl group may be substituted, for example, by hydroxy, $C_1$ to $C_4$ alkoxy, halogen (preferably chlorine or fluorine), cyano, tri($C_1$–$C_{15}$ hydrocarbyl)silyl, or primary, secondary or tertiary amino.

In a linkage of formula I, where $R^1$ is $R^1_a$, —$OR^1_a$ or —$SR^1_a$, $R^1_a$ as $C_1$ to $C_{10}$ alkyl may be, for example, methyl, ethyl, n-propyl, isopropyl, n-butyl, isobutyl, pentyl, hexyl, octyl, nonyl or decyl, preferably $C_1$ to $C_4$ alkyl; $R^1_a$ as $C_2$ to $C_{10}$ alkenyl may be vinyl, allyl, methallyl, 1-propenyl, isopropenyl, 2-butenyl, 1-butenyl, isobutenyl, pentenyl, hexenyl, octenyl or decenyl, preferably $C_2$ to $C_5$ alkenyl; $R^1_a$ as $C_3$ to $C_8$ cycloalkyl may be, for example, cyclopropyl, cyclobutyl, cyclopentyl, methylcyclopentyl, cyclohexyl, methylcyclohexyl, dimethylcyclohexyl, cycloheptyl or cyclooctyl, preferably $C_5$ to $C_8$ cycloalkyl; $R^1_a$ as $C_6$ to $C_{10}$ aryl may be, for example, phenyl, o-tolyl, m-tolyl, p-tolyl, o-xylyl, m-xylyl, p-xylyl or naphthyl, preferably $C_6$ to $C_8$ aryl; $R^1_a$ as $C_7$ to $C_{13}$ aralkyl may be, for example, benzyl, 4-methylbenzyl, 2-phenylethyl, 2-phenylpropyl, 3-phenylpropyl or diphenylmethyl, preferably $C_7$ to $C_9$ aralkyl. $R^1$ as —$NHR^1_b$ may be $C_1$ to $C_{10}$ alkylamino, for example, methylamino, ethylamino, isopropylamino, butylamino, pentylamino, hexylamino, octylamino or decylamino, preferably $C_1$ to $C_4$ alkylamino; $C_2$ to $C_{10}$ alkenylamino, for example allylamino, methallylamino, 1-propenylamino, isopropenylamino, isobutenylamino, hexenylamino, octenylamino or decenylamino, preferably $C_3$ to $C_5$ alkenylamino; $C_3$ to $C_8$ cycloalkylamino, for example, cyclopropylamino, cyclobutylamino, cyclopentylamino, cyclohexylamino, cycloheptylamino, cyclooctylamino or dimethylcyclohexylamino, preferably $C_5$ to $C_8$ cycloalkylamino; $C_6$ to $C_{10}$ arylamino, for example phenylamino, ortho-, meta- or para-tolylamino, ortho-, meta- or para-xylylamino or naphthylamino, preferably $C_6$ to $C_8$ arylamino; $C_7$ to $C_{13}$ aralkylamino, for example benzylamino, 4-methylbenzylamino, 2-phenylethylamino, 3-phenylpropylamino or diphenylmethylamino, preferably $C_7$ to $C_9$ aralkylamino. $R^1$ as —$NR^1_bR^1_c$ may be di($C_1$ to $C_{10}$ alkyl)amino, for example, dimethylamino, diethylamino, methylethylamino, diisopropylamino, dibutylamino or dioctylamino, preferably di($C_1$ to $C_4$ alkyl) amino; N,N-di($C_2$–$C_{10}$ alkenyl)amino, for example diallylamino, dimethallylamino, allylmethallylamino, dipropenylamino, dibutenylamino, dipentenylamino, dihexenylamino, dioctenylamino or didecenylamino, preferably di($C_3$–$C_5$ alkenyl) amino; N,N-di($C_3$–$C_8$ cycloalkyl)amino, for example dicyclopropylamino, cyclopropylcyclopentylamino, dicyclobutylamino, dicyclopentyl amino, dicyclohexylamino, dicycloheptylamino or dicyclooctylamino, preferably N,N-di($C_5$–$C_8$ cycloalkyl) amino; N-$C_3$–$C_8$ cycloalkyl-N-$C_1$–$C_{10}$ alkylamino, for example N-cyclopentyl-N-methylamino, N-cyclopentyl-N-ethylamino, N-cyclohexyl-N-methylamino, N-cyclohexyl-N-ethylamino, preferably N-($C_5$–$C_8$ cycloalkyl)-N-$C_1$–$C_4$ alkylamino; N-$C_6$–$C_{10}$-aryl-N-$C_1$–$C_{10}$ alkylamino, preferably N-$C_6$–$C_8$-aryl-$C_1$–$C_4$ alkylamino, for example N-phenyl-N-methylamino, N-tolyl-N-methylamino or N-phenyl-N-ethylamino; N, N-di($C_7$–$C_{13}$ aralkyl)amino, for example dibenzylamine, di(4-methylbenzyl)amine, di(phenylethyl)amino or di(phenylpropyl)amino, preferably N,N-di($C_7$–$C_9$ aralkyl)amino; or N-$C_7$–$C_{13}$ aralkyl-N-$C_1$–$C_{10}$ alkylamino, preferably N-$C_7$–$C_9$ aralkyl-N-$C_1$–$C_4$ alkylamino, for example N-benzyl-N-methylamino or N-benzyl-N-ethylamino or a radical of a five- or six-membered N-heterocycle linked through the nitrogen atom to the indicated phosphorus atom in formula I, for example 1-pyrrolidinyl, 1-piperidyl, 1-piperazinyl or morpholino. Any of the above groups may be unsubstituted or substituted as hereinbefore described.

In certain preferred embodiments, $R^1$ is hydrogen, hydroxy, $O^{31}$, SH, $S^{31}$, an unsubstituted or substituted $C_1$ to $C_4$ alkyl or phenyl group, a group of formula —$OR^1_a$ where $R^1_a$ is an unsubstituted or substituted $C_1$ to $C_4$ alkyl, $C_3$ to $C_5$ alkenyl, $C_5$ to $C_8$ cycloalkyl or $C_7$ to $C_9$ aralkyl group, or a group of formula —$SR^1_a$ where $R^1_a$ is an unsubstituted or substituted $C_1$ to $C_4$ alkyl or phenyl group, optional substituents being as hereinbefore described. In some especially preferred embodiments, $R^1$ is hydrogen, hydroxy, $O^{31}$, SH, $S^{31}$, methoxy, ethoxy or 2-cyanoethoxy.

Where $R^1$ in formula I is $O^-$, the oligonucleotide analogue of the invention may be in the form of a pharmaceutically acceptable salt, for example metal salt, preferably an alkali metal salt, or an unsubstituted or substituted ammonium salt, for example a mono-, di- or tri-$C_1$ to $C_{10}$ alkyl- or hydroxyalkyl-ammonium salt, a N-ethylpiperidinylium salt or a $N,N^1$-dimethylpiperazinylium salt. In especially preferred embodiments where $R^1$ is $O^-$, the oligonucleotide analogue is in the form of the sodium or ammonium salt.

Where the phosphorus atom in formula I is a chiral centre, differences may be observed in hybridisation and nuclease resistance properties and in biological efficacy depending on the stereochemistry at phosphorus.

An oligonucleotide analogue of the invention may be represented by the formula V—L—(V—L)$_n$V where n is a number from 8 to 198, each V is independently a residue of a natural or synthetic nucleoside, each of the n+2 residues V being the same as, or different from, an adjacent residue V, and each L is an internucleoside linkage, each of the n+1 linkages L being the same as, or different from, an adjacent linkage L, at least one L being of formula I.

The present invention also provides a method of preparing an oligonucleotide analogue having at least one internucleoside linkage of formula I, for example an oligonucleotide having 2 to 200 nucleoside units, such as an oligonucleotide analogue as hereinbefore described, which comprises (i) carrying out a coupling reaction or successive coupling reactions between (A) a natural or synthetic nucleoside or oligonucleotide having a 5'-hydroxyl group and (B) a natural or synthetic nucleoside or dinucleotide having at the 3'-position thereof a group reactive with said 5'-hydroxyl group until an oligonucleotide having the desired number of nucleosides is obtained, in at least one of said coupling reactions (B) being a nucleoside of formula

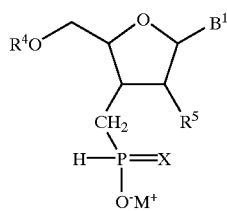

II where $B^1$ is a nucleoside base radical, $R^4$ is a hydroxy-protecting group, $R^5$ is hydrogen, hydroxy or a 2' modifying atom or group, $M^+$ is a metal or unsubstituted or substituted ammonium ion or a cation of a heterocyclic base such as pyrrolidine, piperidine, N-ethylpiperidine, $N,N^1$-dimethylpiperazine, morpholine or 1,8 diazabicyclo[5.4.0]undec-7-ene (DBU) and X is oxygen or sulphur, and being reacted with (A) in the presence of a sterically hindered organic acid halide or anhydride to form an oligonucleotide analogue having a phosphinate internucleoside linkage of formula

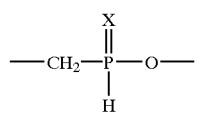

IA where X is oxygen or sulphur, and (ii)(a) oxidising the phosphinate linkage or (b) sulphurising the phosphinate linkage, or (c) reacting the phosphinate linkage with a compound of formula $R^1_aY$ where $R^1_a$ is as hereinbefore defined and Y is a leaving atom or group or (d) oxidising and reacting the phosphinate linkage with an alcohol of formula $R^1_aOH$ or an amine of formula $R^1_bNH_2$ or $R^1_bR^1_cNH$ where $R^1_a$, $R^1_b$ and $R^1_c$ are as hereinbefore defined, or (e) silylating the phosphinate linkage and reacting the silylated linkage with a thioalkylating or thioarylating agent to give a phosphinate linkage of formula I where $R^1$ is $—SR^1_a$ where $R^1_a$ is as hereinbefore defined.

The hereinbefore defined method may be carried out in solution or on a solid carrier, for example using known procedures for oligonucleotide synthesis. The oligonucleotide analogue obtained by this method may be further reacted to replace the protecting group $R^4$ by hydrogen or, where $R^4$ is on a terminal nucleoside in the oligonucleotide analogue, by a 5' modifying group as hereinbefore described.

Oligonucleotide analogues of the invention may be prepared by solid phase synthesis, for example using H-phosphonate, phosphotriester or phosphoramidite methods, or a mixture of two or more thereof, for example automatically using commercially available nucleic acid synthesisers. A solid phase synthetic method may comprise carrying out successive coupling reactions (i) as hereinbefore described and step (ii) as hereinbefore described with the nucleoside or oligonucleotide (A) attached to the solid support, then (iii) detaching the oligonucleotide from the solid support and removing protecting groups to give an oligonucleotide having a terminal 5' free hydroxyl group and (iv) optionally reacting the 5' free hydroxyl group to introduce a modifying group at the terminal 5' position. In the nucleoside of formula II, $B^1$ may be a purine or pyrimidine base or analogue thereof as hereinbefore described. Compounds where $B^1$ is a natural nucleoside base, more preferably pyrimidine base, especially thymine, are preferred. $R^4$ may be any hydroxy-protecting group capable of protecting the 5' hydroxyl group against undesired reaction. Such groups are well known and include $C_1$ to $C_{10}$ aliphatic, e.g. alkyl, groups; $C_3$ to $C_8$ cycloaliphatic, e.g. cycloalkyl, groups; $C_6$ to $C_{10}$ aromatic, e.g. aryl, groups; $C_7$ to $C_{40}$ araliphatic, e.g. aralkyl or $C_1$ to $C_4$ alkoxy-substituted aralkyl, groups; groups of formula $—COR^6$ or $—SO_2R^6$ where $R^6$ is a $C_1$ to $C_{10}$ aliphatic group, a $C_3$ to $C_8$ cycloaliphatic group, a $C_6$ to $C_{10}$ aromatic group or a $C_7$ to $C_{40}$ araliphatic group; and tri($C_1$–$C_{15}$ hydrocarbyl)silyl groups. Preferably $R^4$ is a 5' protecting group conventionally used in oligonucleotide synthesis, especially a methoxytrityl, dimethoxytrityl or tris tert-butyltrityl group. $R^5$ as a 2' modifying atom or group may be such an atom or group as hereinbefore described; preferably $R^5$ is hydrogen. $M^+$ may be, for example, an alkali metal ion or, preferably, an unsubstituted ammonium ion, a mono-di- or tri-$C_1$ to $C_{10}$ alkyl- or hydroxyalkyl-ammonium ion or a cation of a heterocyclic base such as pyrrolidine, piperidine, N-ethylpiperidine, N,N-dimethylpiperazine, morpholine or DBU. An especially preferred $M^+$ is a triethylammonium ion.

Preferred stereoisomers of nucleosides of formula II are those of formula

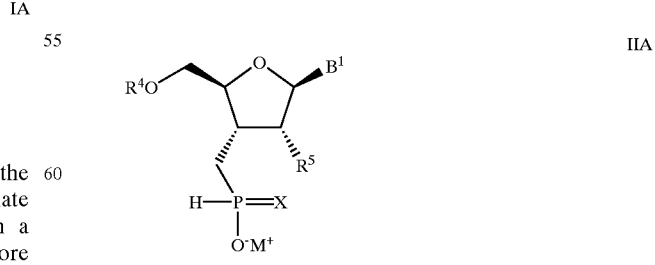

IIA where $B^1$, $R^4$, $R^5$, X and $M^+$ are as hereinbefore defined.

Nucleosides of formula II may be prepared by a) reacting a compound of formula

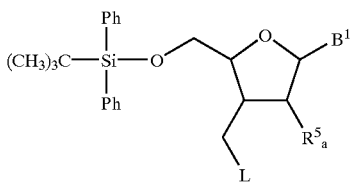

III where $B^1$ and $R^4$ are as hereinbefore defined, $R^5_a$ is hydrogen, fluorine or $—OR^2$ where $R^2$ is as hereinbefore defined and L is a leaving atom or group, preferably an iodine atom, with ethyl (1,1-diethoxyethyl)phosphinate in the presence of a base such as potassium bis(trimethylsilyl) amide in tetrahydrofuran (THF) at −80° C. to 40° C. to give a compound of formula

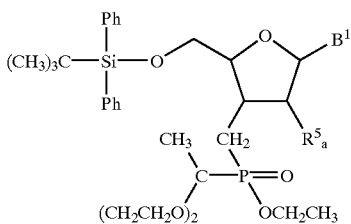

IV where $B^1$ and $R^5_a$ are as hereinbefore defined, b) reacting the compound of formula IV with trimethylsilyl chloride in chloroform containing 1% ethanol under argon at ambient temperature to replace the protecting ketal group attached to phosphorus by hydrogen, c) reacting the product from b) with acetone in the presence of titanium (IV) isopropoxide in dry THF at ambient temperature to give a compound of formula

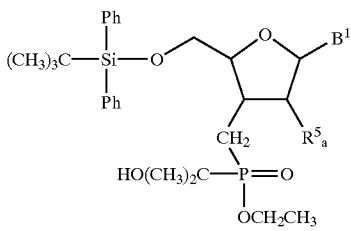

V d) reacting the compound of formula V with tetra-n-butylammonium fluoride and acetic acid in THF at ambient temperature to remove the tert-butyldiphenylsilyl protecting group, e) reacting the resulting 5'-hydroxy-containing compound with a compound of formula $R^4Y$, where $R^4$ is as hereinbefore defined and Y is halogen, in the presence of an organic base to give a compound of formula

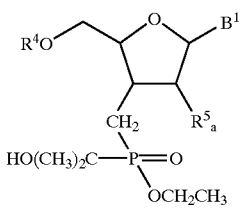

VI where $B^1$, $R^4$ and $R^5_a$ are as hereinbefore defined, f) reacting the compound of formula VI with an alkali metal methoxide in anhydrous methanol, or with DBU in water, at ambient temperature to remove the ethyl group and replace the $—C(CH_3)_2$ OH group by hydrogen, g) if desired, treating the product with ammonia or an amine to form the corresponding unsubstituted or substituted ammonium salt, and h) if desired, sulphurising the product to give a nucleoside of formula II in which X is sulphur, for example by reaction with pivaloylchloride followed by $(CH_3)_3$ Si—S—Si$(CH_3)_3$ using the procedure described in J. Org. Chem. 1995, 60, 8241.

The compounds of formulae IV, V or VI may be reacted to introduce, or introduce a different, modifying atom or group $R^5$ at the 2' position using, for example, a conventional procedure for introducing such a 2' modifying atom or group into a nucleoside.

Compounds of formula III may be prepared by reducing an aldehyde of formula

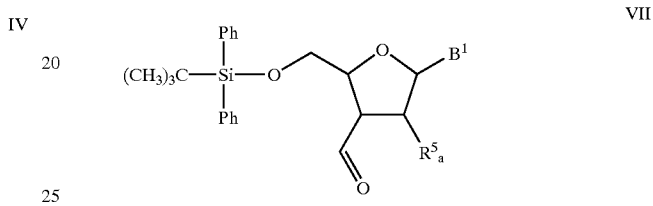

VII where $B^1$ and $R^5_a$ are as hereinbefore defined, prepared according to the method described in WO 92/20823, to the corresponding alcohol by reaction with $NaBH_4$ in anhydrous ethanol at ambient temperature and reacting the alcohol with methyltriphenoxyphosphonium iodide in the presence of 2,6-lutidine in dry dimethyl formamide at 0° C. to 30° C.

Ethyl(1,1-diethoxyethyl)phosphinate may be prepared as described in EP 0 307 362.

In a typical procedure using solid phase synthesis, a natural or synthetic nucleoside having a protected 5' hydroxyl group is covalently linked at the 3' position to an inert silica-based support, such as controlled pore glass (CPG), containing long chain alkylamino groups, using a linker such as succinic anhydride to give a 3'-terminal nucleoside attached to the solid support. The solid support may also contain groups to act as 3' terminal modifying groups for the desired oligonucleotide. The protecting group, for example a dimethoxytrityl group, on the 5' hydroxy of the attached terminal nucleoside is then removed to give a free 5' hydroxy group. The terminal nucleoside is then coupled with a natural or synthetic nucleoside or dinucleotide (B) having a protected, e.g. dimethoxytrityl-protected, 5' hydroxyl group and, at the 3' position a group which is reactive with, or activatable to be reactive with, the 5' free hydroxyl group on the terminal nucleoside to give a dimeric oligonucleotide (or, where (B) is a dinucleotide, a trimeric oligonucleotide) attached to the solid support. After the 5' protecting group on the attached oligonucleotide has been removed, the reaction cycle with a natural or synthetic 5' protected nucleoside or dinucleotide (B) having a 3' reactive group is repeated until an oligonucleotide having the desired number of nucleosides has been synthesised.

For the formation of internucleoside linkages other than those of formula I, the reactive group, or the group activatable to be reactive, at the 3' position of the nucleoside or dinucleotide (B) is chosen in accordance with conventional oligonucleotide synthesis procedures and may be, for example, an H-phosphonate group, a phosphoramidite group or a phosphodiester group. The coupling reactions and, where necessary, subsequent oxidation, sulphurisation or other treatment, to form these internucleoside linkages, for example phosphotriester, phosphorothioate or phosphorodithioate linkages, may be carried out using conventional procedures.

In preparing an oligonucleotide analogue of the invention, at least one of the coupling reactions is carried out using as (B) a nucleoside of formula II, which is reacted with the nucleoside or oligonucleotide (A), which in solid phase synthesis is attached to the solid support, in the presence of a sterically hindered organic acid halide or anhydride, for example pivaloyl chloride, adamantoyl chloride, 2,4,6-triisopropylbenzenesulphonyl chloride, diphenylphosphinic chloride, bis(2-oxo-3-oxazolidinyl) phosphinic chloride, 2-chloro-2-oxo-5,5-dimethyl-1,3,2-dioxaphosphinane or bis (pentafluorophenyl) anhydride. Preferably, the reaction is carried out in the presence of a heterocyclic base having a tertiary nitrogen atom in the ring or an oxide of such a base, for example, pyridine, quinoline, N-methylimidazole or pyridine-N-oxide and, especially, an organic solvent such as acetonitrile. The coupling reaction may be carried out at ambient or moderately elevated temperatures, for example up to 50° C.

The phosphinate internucleoside linkage of formula IA formed by a coupling reaction using as (B) a nucleoside of formula II may be oxidised or sulphurised before the next coupling reaction is carried out or, preferably, after an oligonucleotide analogue with the desired number of nucleosides has been synthesised, when it may be oxidised or sulphurised together with one or more other phosphinate internucleoside linkages formed by other coupling reactions using a nucleoside of formula II or phosphite linkages formed by coupling reactions using a 3' H phosphonate-substituted nucleoside. Oxidation (ii)(a) may be effected by treatment with iodine and water, or with tert-butyl hydroperoxide, for example using conventional procedures for oxidation of phosphite internucleoside linkages. Sulphurisation (ii)(b) may be effected by treatment with sulphur in the presence of a tertiary amine in an organic solvent, usually carbon disulphide, for example using known procedures.

The reaction (ii)(c) of the phosphinate internucleoside linkage of formula IA with a compound of formula $R^1_a Y$ where $R^1_a$ and Y are as hereinbefore defined, Y preferably being a halogen atom or a trifluoromethanesulphonate group, may be carried out, where $R^1_a$ is alkyl, cycloalkyl or aralkyl, using known alkylation procedures, for example by reacting the phosphinate linkage of formula IA with $R^1_a Y$ where Y is halogen in the presence of a strong base such as sodium hydride. Where $R^1_a Y$ is an alkenyl or aryl halide or triflate, the reaction between the phosphinate linkage and $R^1_a Y$ may be carried out using known procedures, for example in the presence of a palladium catalyst such as $Pd(PPh_3)_4$ and a tertiary amine, for example as described by Y.Xu et al, Tetrahedron Lett., 30, 949(1989) or K. S. Petrakis et al, J. Am. Chem. Soc., 109, 2831 (1987).

The oxidative reaction (ii)(d) of the phosphinate internucleoside linkage of formula IA with an alcohol of formula $R^1_a OH$, before the next coupling reaction or after an oligonucleotide with the desired number of nucleosides has been synthesised, may be carried out by reaction with an oxidant such as iodine, carbon tetrachloride or bromotrichloromethane in the presence of the alcohol $R^1_a OH$ and a base such as pyridine, for example under conventional conditions for oxidation of phosphite internucleoside linkages.

The oxidative reaction (ii)(d) of the phosphinate internucleoside linkage of formula IA may be effected, before the next coupling reaction or after an oligonucleotide with the desired number of nucleosides has been synthesised, with an amine of formula $R^1_b NH_2$ or $R^1_b R^1_c NH$ where $R^1_b$ and $R^1_c$ are as hereinbefore defined, and carbon tetrachloride or bromotrichloromethane or iodine to give an oligonucleotide analogue of the invention in which $R^1$ is $—NHR^1_b$ or $—NR^1_b R^1_c$ respectively. The reaction may be carried out using known conditions and procedures for Atherton-Todd reactions.

The reaction (ii)(e) of the phosphinate linkage of formula IA may be carried out by silylating the linkage using known silylation procedures, for example using a trialkylsilyl halide and a base such as triethylamine, and reacting the silylated linkage with a thioalkylating or thioarylating agent such as a thiosulphonate of formula $ArSO_2 SR^1_a$ where $R^1_a$ is as hereinbefore defined and Ar is an aromatic group such as phenyl or tolyl. Suitable procedures for this reaction are described by W. K. D. Brill, Tetrahedron Lett, 36, 703 (1995).

It will be apparent to those skilled in the art that in reacting the phosphinate linkage of formula IA to replace the hydrogen atom attached to phosphorus by a group $R^1$ having a reactive substituent such as amino, the substituent should be protected during the reaction to introduce $R^1$ if it is reactive under the conditions of that reaction and subsequently deprotected.

When an oligonucleotide analogue having the desired number of nucleosides has been synthesised on a solid support, it is detached from the solid support, for example using conventional methods such as treatment with concentrated aqueous ammonia, which treatment also removes a protecting group which may have been present on an exocyclic nitrogen atom in one or more of the nucleosides used in the synthesis of the oligonucleotide, before or after treatment to remove hydroxy-protecting groups such as dimethoxytrityl groups, which may also be carried out using conventional methods, for example by treatment with an aqueous organic acid such as trifluoroacetic acid.

Before or after detachment of the oligonucleotide from the solid support, the terminal 5' hydroxyl generated on deprotection can be reacted to introduce a 5' terminal modifying group, such as a phosphate group or other 5' modifying group as hereinbefore described, for example using the procedures described by Beaucage and Iyer, Tetrahedron 49, 1925–63 (1993).

In a modification of the synthetic method hereinbefore described, the nucleoside of formula II may be replaced by a dinucleotide of formula

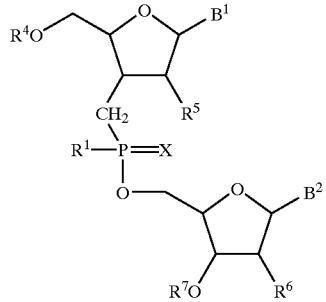

VIII where $B^1$, $R^1$, $R^4$ and $R^5$ are as hereinbefore defined, $B^2$ is a nucleoside base radical, which may be a radical of a natural or synthetic nucleoside base as hereinbefore described for $B^1$, $R^6$ is hydrogen, hydroxy or a 2' modifying atom or group as hereinbefore defined for $R^5$, and $R^7$ is a group reactive with, or activatable to be reactive with, a 5' hydroxyl group in a nucleoside.

In this modification, the group $R^7O$ in the dinucleotide of formula VIII may be a H-phosphonate group, in which case the dinucleotide of formula VII may be reacted with the nucleoside or oligonucleotide (A), which in solid phase synthesis is attached to the solid support, in the presence of a sterically hindered organic acid halide, for example using conventional procedures for oligonucleotide synthesis using 3' H-phosphonates, to form a phosphite internucleoside linkage which may then be oxidised, sulphurised or reacted with a compound of formula $R^1_aY$ or subjected to another of the reactions (ii)(a) to (ii)(e) as hereinbefore described for the phosphinate internucleoside linkage of formula IA formed by reaction of the nucleoside of formula II with (A).

In this modification, the group $R^7O$ in the dinucleotide of formula VIII may alternatively be a phosphoramidite group, in which case the dinucleotide of formula VIII may be reacted with the nucleoside or oligonucleotide (A), for example using conventional procedures for oligonucleotide synthesis using 3' phosphoramidites.

In another alternative embodiment of this modification, the group $R^7O$ in the dinucleotide of formula VIII may be a phosphodiester group, in which case the dinucleotide of formula VIII may be reacted with the nucleoside or oligonucleotide (A), for example using conventional procedures for oligonucleotide synthesis using 3' phosphodiesters.

Dinucleotides of formula VIII may be prepared by reacting a nucleoside of formula II with a nucleoside of formula

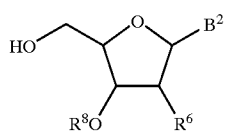

IX where $B^2$ and $R^6$ are as hereinbefore defined and $R^8$ is a hydroxy-protecting group, in the presence of a dehydrating coupling reagent e.g. a carbodiimide or a sterically hindered organic acid halide or anhydride, to give a dinucleotide of formula

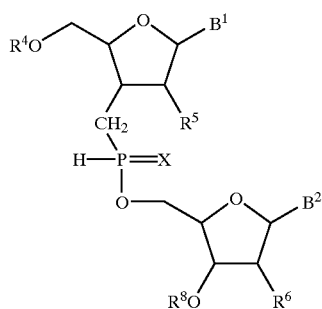

X and, optionally after subjecting the internucleoside linkage in formula X to any of reactions (ii)(a) to (ii)(e) as hereinbefore described, converting the $R^8O$— group into a $R^7O$— group.

The hydroxy-protecting group $R^8$ may be chosen from groups hereinbefore specified for $R^4$. Preferably $R^8$ is a 3' protecting group conventionally used in nucleoside chemistry, especially a tert-butyldiphenylsilyl group.

Nucleosides of formula IX are 3' protected natural or synthetic nucleosides which may have hydrogen, hydroxy or a 2' modifying atom or group at the 2' position. Such nucleosides are known or may be prepared by known methods.

The reaction between the nucleoside of formula II and the nucleoside of formula IX in the presence of a sterically hindered organic acid halide is preferably carried out in the presence of a heterocyclic base or oxide thereof and an organic solvent as hereinbefore described for the reaction of the nucleoside of formula II with the nucleoside or oligonucleotide (A).

The conversion of the group $R^8O$— into a group $R^7O$— where $R^8$ and $R^7$ are as hereinbefore defined may be carried out using conventional methods for converting a protected 3' hydroxyl group into a group reactive with, or activatable to be reactive with, a 5' hydroxyl group, such as a H-phosphonate, phosphoramidite or phosphodiester group. For example, the protecting group $R^8$ may be removed to generate a free 3' hydroxyl, which may then be reacted with an aliphatic bis(N,N-dialkyl)phosphoramidite such as 2-cyanoethyl bis(N,N-diisopropyl)phosphordiamidite to form a 3' phosphoramidite group.

Dinucleotides of formulae VIII where one or each of $R^5$ and $R^6$ is 2' modifying atom or group as hereinbefore defined, particularly a group of formula —$OR^2$ as hereinbefore defined, are novel. Dinucleotides of formula X are novel. Thus the invention also provides novel dinucleotides of formula

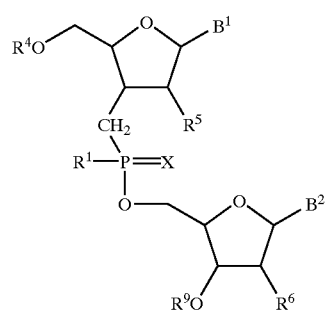

XI where $B^1$, $B^2$, $R^1$, $R^4$ are as hereinbefore defined, $R^5$ and $R^6$ are as hereinbefore defined except that where $R^1$ is other than hydrogen at least one of $R^5$ and $R^6$ is a 2' modifying atom or group as hereinbefore defined, and $R^9$ is $R^7$ or $R^8$ as hereinbefore defined, especially those where $R^5$ is hydrogen or hydroxy and $R^6$ is a 2' modifying atom or group as hereinbefore defined, particularly a group of formula —$OR^2$ as hereinbefore defined.

Dinucleotides of formula VIII where $R^1$ is $C_1$ to $C_{10}$ alkoxy may also be prepared by reacting a nucleoside of formula

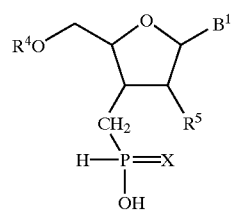

XII where $B^1$, $R^4$ and $R^5$ are as hereinbefore defined, with a nucleoside of formula IX in the presence of a tertiary amine such as dimethylaminopyridine and a dehydrating agent such as dicyclohexylcarbodiimide (DCC), to give a dinucleotide of formula X, which is then treated as hereinbefore described to give a dinucleotide of formula VIII. The reaction between the nucleosides of formulae XII and IX may be carried out in a solvent such as THF at ambient temperature.

Nucleosides of formula XII can be prepared by treating nucleosides of formula II (salt forms of acids of formula XII) with acid using conventional procedures.

Oligonucleotides having at least one internucleoside linkage of formula I, for example an oligonucleotide having 2 to 200 nucleoside units, such as an oligonucleotide analogue as hereinbefore described, may also be prepared by subjecting a nucleoside having a protected 5' hydroxy group and, at the 3' position, a group of formula

XIII

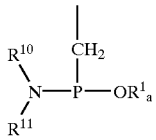

where $R^1_a$ is as hereinbefore defined, $R^{10}$ and $R^{11}$ are each independently an unsubstituted or substituted $C_1$ to $C_{10}$ alkyl, $C_2$ to $C_{10}$ alkenyl, $C_4$ to $C_{10}$ cycloalkylalkyl, $C_6$ to $C_{10}$ aryl or $C_7$ to $C_{13}$ aralkyl group, or $R^{10}$ is said group and $R^{11}$ is hydrogen, or $R^{10}$ and $R^{11}$ together with the nitrogen atom to which they are attached denote a five- to thirteen-membered heterocyclic ring, to a nucleoside coupling reaction with a natural or synthetic nucleoside or oligonucleotide having a free 5' hydroxy group, to form an oligonucleotide precursor having an internucleoside linkage of formula

XIV

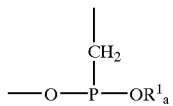

where $R^1_a$ is as hereinbefore defined, and converting the precursor into an oligonucleotide having an internucleoside linkage of formula

XV

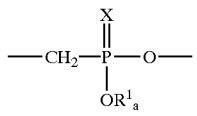

where $R^1_a$ is as hereinbefore defined and X is oxygen or sulphur by oxidising the precursor to give an oligonucleotide having an internucleoside linkage of formula XV where X is oxygen or sulphurising the precursor to give an oligonucleotide having an internucleoside linkage of formula XV where X is sulphur.

The reaction to form the precursor having a linkage of formula XIV may be carried out in the presence of an amine-protonating coupling catalyst (activating agent) such as tetrazole or 5-(4-nitrophenyl)tetrazole. The reaction may be carried out at −20 to 50° C., preferably at room temperature. The oxidation or sulphurisation of the resulting precursor may be effected by methods used for oxidation or sulphurisation respectively of phosphite internucleoside linkages. Thus oxidation may be effected by treatment with iodine and water, or with a hydroperoxide such as tert-butyl hydroperoxide, for example using conditions and procedures known for oxidation of phosphite internucleoside linkages in oligonucleotide synthesis. Sulphurisation may be effected by treatment with sulphur in the presence of a tertiary amine in an organic solvent, usually carbon disulphide, by treatment with [3H] 1,2-benzodithiol-3-one-1,1-dioxide (Beaucage reagent) or by treatment with tetraethylthiuram, for example using procedures known for sulphurisation of phosphite internucleoside linkages.

Nucleosides having a protected 5' hydroxy group and, at the 3' position, a group of formula XIII, may be prepared by reacting a nucleoside having a protected 5' hydroxy group and, at the 3' position, a group of formula

XVI

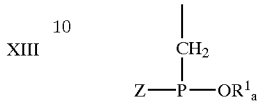

where $R^1_a$ is as hereinbefore defined and Z is halogen, with a compound of formula

XVII

where $R^{10}$ and $R^{11}$ are as hereinbefore defined. The reaction may be carried out in an organic solvent, for example a halogenated hydrocarbon such as chloroform, in the presence of a tertiary nitrogen base such as pyridine, and at a temperature from −78° C. to 50° C., preferably from −30° C. to 25° C.

Nucleosides having a protected 5' hydroxy group and, at the 3' position, a group of formula XVI may be prepared by non-oxidative halogenation of a nucleoside having a protected 5' hydroxy group and, at the 3' position, a group of formula

XVIII

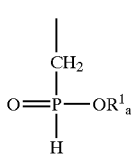

The non-oxidative halogenation may be carried out by reaction with a non-oxidative halogenating agent, for example a halophosphorane such as triphenyldichlorophosphorane or dichlorotris(2,4,6-tribromophenoxy) phosphorane in the presence of a base, preferably a tertiary nitrogen base such as pyridine, in an organic solvent, which may be pyridine but is preferably a halohydrocarbon such as chloroform, at a temperature from −20° C. to 60° C., preferably from 0° C. to 50° C.

Nucleosides having a protected 5' hydroxy group, and at the 3' position, a group of formula XVIII may be prepared as described in WO 96/08503.

When the oligonucleotide having a linkage of formula XV is formed on a solid support, it may be treated to remove the 5' protecting group and the resulting 5' hydroxy-terminated oligonucleotide subjected to successive coupling cycles with a natural or synthetic nucleoside or oligonucleotide having a protected 5' hydroxyl group and, at the 3' position, a group reactive with, or activatable to be reactive with, the free 5' hydroxy group on the deprotected oligonucleotide attached to the solid support, until an oligonucleotide of the desired length is obtained. Thus the oligonucleotide having a linkage of formula XV may be coupled with a nucleoside or oligonucleotide having a 3' phosphoramidite, H-phosphonate, phosphodiester group or 3' group of formula XIII and a protected 5' hydroxyl group, to give a chain-extended oligonucleotide which may in turn be further chain extended by further such alternative reactions until an oligonucleotide of the desired length is obtained. Where a nucleoside or oligonucleotide having a 3' phosphoramidite, H-phosphonate or phosphodiester group is used, the coupling reaction may be carried out using procedures known in oligonucleotide synthesis. Where a nucleoside having a 3' group of formula XIII is used, the coupling reaction may be carried out as hereinbefore described. Thus, where a 3' phosphoramidite or a 3' group of formula XIII is used, a coupling cycle involves an oxidation or sulphurisation while where a 3'H-phosphonate is used, oxidation or sulphurisation is effected after chain extension is complete, and where a 3' phosphodiester is used no oxidation is required.

The oligonucleotide analogues of the invention can be used in therapeutics, for example in the treatment of a human or other animal suffering from a disease which is modulated by a protein, or in the treatment of viruses such as influenza, herpes and HIV. Accordingly, the present invention also provides a pharmaceutical composition comprising as active ingredient an oligonucleotide analogue of the invention. Optimum dosages and treatment schedules can readily be determined by those skilled in the art. When administered to mammals of about 70 kg weight, the dose can be, for example, 0.01 to 1000 mg per day. It will generally be preferred to administer therapeutic agents in accordance with the invention internally, for example orally, by inhalation, intravenously or intramuscularly. Other methods of administration, such as transdermal, topical or interlesional methods, and by inclusion in suppositries, can also be useful. Use in conduction with pharmacologically acceptable carriers is preferred for some therapeutic treatments.

The oligonucleotide analogues according to the invention have a surprisingly high stability to degradation by nucleases. A very good pairing with complementary nucleic acid strands, particularly of the RNA type, is also observed. The oligonucleotide analogues according to the invention are therefore particularly suitable for antisense technology, i.e. for inhibition of the expression of undesired protein products due to the binding to suitable complementary nucleotide sequence in nucleic acids (see EP 0 266 099, WO 87/07300 and WO 89/08146). They can be employed for the treatment of infections and diseases, for example by blocking the expression of bioactive proteins at the nucleic acid stage (for example oncogenes). The oligonucleotide analogues according to the invention are also suitable as diagnostics and can be used as gene probes for the detection of viral infections or of genetically related diseases by selective interaction at the single or double-stranded nucleic acid stage. In particular—due to the increased stability to nucleases—diagnostic use is not only possible in vitro but also in vivo (for example tissue samples, blood plasma and blood serum). Use possibilities of this type are described, for example, in WO 91/06556.

The novel dinucleotides of formula XI can be used as pharmaceuticals, for example as antiviral agents.

The pharmacologically active oligonucleotide analogues and dinucleotides according to the invention can be used in the form of parenterally administrable preparations or of infusion solutions. Solutions of this type are preferably isotonic aqueous solutions or suspensions, it being possible to prepare these before use, for example in the case of lyophilised preparations which contain the active substance on its own or together with a carrier, for example mannitol. The pharmaceutical preparations can be sterilised and/or contain excipients, for example preservatives, stabilisers, wetting and/or emulsifying agents, solubilisers, salts for regulating the osmotic pressure and/or buffers. The pharmaceutical preparations, which if desired can contain further pharmacologically active substances such as, for example, antibiotics, are prepared in a manner known per se, for example by means of conventional dissolving or lyophilising processes, and contain about 0.1% to 90%, in particular from about 0.5% to about 30%, for example 1% to 5% of active substance(s).

This invention is illustrated by the following Examples.

Compounds used in the Examples, and precursors thereof, are prepared as follows. All $^{31}P$ data for these compounds and those of the Examples are for $^1H$ decoupled.

Compound A

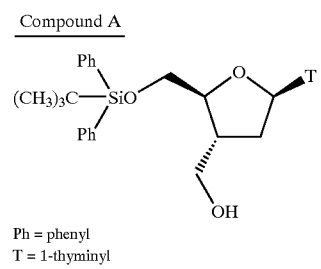

Ph = phenyl
T = 1-thyminyl

To a solution of an aldehyde of formula XIII where $R^2$ is hydrogen, $B^1$ is I-thyminyl and $R^1$ is tert-butyl diphenylsilyl, prepared as described in WO 92/20823, (11.2 g 23 mmol) in anhydrous ethanol (120 ml) at room temperature is added $NaBH_4$ (865 mg, 23 mmol) portionwise over 5 minutes. After 1 hour, the reaction mixture is quenched with water, diluted with ethylacetate (500 ml) and washed with water (2×50 ml). After back extraction of the aqueous phase, the combined organic phase is dried ($MgSO_4$) and concentrated to give Compound A as a white solid.

$^1H$ nmr ($CDCl_3$, 400 MHz) δ9.10 (1H, s, NH) 7.65 (4H, d, Ar 4×CH ortho), 7.40 (7H, m, Ar 4×CH meta, 2×CH para+H6) 6.13 (1H, t, H1') 4.00 (1H, dd, H5'), 3.93 (1H, m, H4') 3.82 (1H, dd, H5'), 3.62 (2H, m, $CH_2$OH) 2.60 (1H, m, H3'), 2.32 (1H, m, H2'), 2.12 (1H, m, H2') 1.62 (3H, s, T-$CH_3$) and 1.10 (9H, s, $^tBu$) ppm.

Compound B

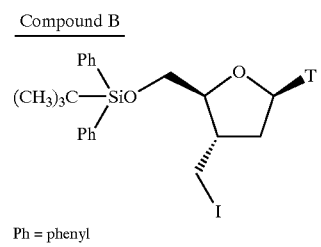

Ph = phenyl
T = 1-thyminyl

To a solution of Compound A (9 g, 18.1 mmol) in dry DMF (100 ml) at 0–5° C. is added 2,6-lutidine (4.25 ml, 36.5 mmol) followed by methyltriphenoxyphosphonium iodide (9.45 g, 20.9 mmol). The resulting mixture is allowed to warm to room temperature. After 1 hour the mixture is diluted (200 ml ethyl acetate) and washed with 0.1N $NaS_2O_3$ (2×20 ml), 0.5N Hydrochloric acid (2×20 ml) and water (2×20 ml). Drying, concentration and purification by flash silica column chromatography (gradient elution chloroform:ethylacetate 20:1-7:1) gives Compound B as a white solid.

$^1$H nmr (CDCl$_3$, 400 MHz) δ10.2 (1H, s, NH) 7.66 (4H, d, 4×CH ortho), 7.40 (7H, M, 4×CH meta, 2×CH para+H6) 6.19 (1H, t, H1') 4.02 (1H, dd, H5'), 3.82 (1H, m, H4') 3.78 (1H, dd, H5'), 3.17 (1H, dd, C$\underline{H}_2$I) 3.10 (1H, dd C$\underline{H}_2$I), 2.68 (1H, m, H3'), 2.30 (1H, m, H2'), 2.23 (1H, m, H2') 1.66 (3H, s, CH$_3$-T), 1.10 (9H, s, tBu) ppm.

Compound C

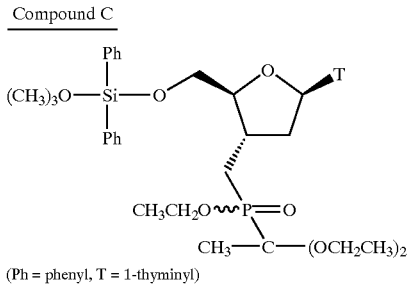

(Ph = phenyl, T = 1-thyminyl)

To a solution of ethyl (1,1-diethoxyethyl)phosphinate (5.51 g, 26.2 mmol) in dry THF (170 ml), under argon, at −78° C. is added a solution of potassium bis(trimethylsilyl) amide (34.6 ml, 0.75M solution in toluene) dropwise over 5 minutes. The resulting solution is stirred at −78° C. for 1 hour. A solution of Compound B (5.0 g, 8.25 mmol) in dry THF (20 ml) is then added dropwise over 5 minutes. Stirring is continued at −78° C. for 1 hour before warming to room temperature over 2 hours. Saturated aqueous ammonium chloride (50 ml) is then added and the whole mixture extracted with ethyl acetate (500 ml). The organic phase is washed with saturated ammonium chloride (2×50 ml) and water (2×50 ml), dried over magnesium sulphate and concentrated. Purification by flash silica column chromatography (eluant ethylacetate:ethanol 30:1) gives Compound C as a 1:1 mixture of diastereoisomers epimeric at phosphorous.

Compound D

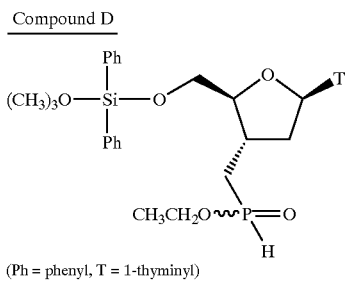

(Ph = phenyl, T = 1-thyminyl)

Trimethylsilylchloride (4.44 ml, 35 mmol) is added dropwise (2 minutes) at room temperature to a stirred solution of Compound C (2.4 g, 3.5 mmol) in chloroform (25 ml) containing ethanol (1%) under argon. After standing at −20° C. for 60 hours, a further portion of trimethylsilylchloride (2.22 ml, 17.5 mmol) is added along with ethanol (200 μl) and the resulting solution stirred at room temperature for 7 hours. Concentration and co-evaporation with chloroform (50 ml) gives a white solid which is purified by flash silica column chromatography (eluant chloroform: ethanol 13:1) to give Compound D as a white solid isolated as a 1:1 mixture of diastereoisomers.

Compound E

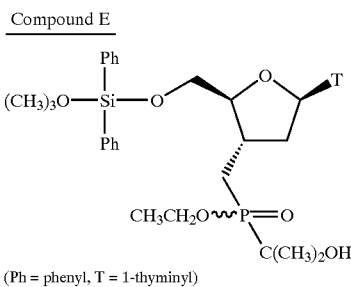

(Ph = phenyl, T = 1-thyminyl)

To a solution of Compound D (1.2 g, 2.1 mmol) in dry THF (30 ml) containing acetone (3.2 ml) is added in titanium (IV) isopropoxide (738 μl, 2.48 mmol). After 15 minutes, concentration and passage through a short column of silica (eluant ethyl acetate:ethanol 4:1) (500 ml) gives Compound E isolated as a mixture of 2 diastereoisomers.

$^{31}$P nmr $^1$H decoupled (CDCl$_3$, 162 MHz) δ55.0, 54.7 ppm.

Found: C, 57.7; H, 7.05; N, 4.05% C$_{32}$H$_{45}$N$_2$O$_7$PSi.2H$_2$O requires C, 57.8; H, 7.4; N, 4.2%

Compound F

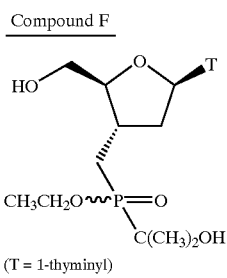

(T = 1-thyminyl)

To a solution of Compound E (1.02 g, 1.62 mmol) and acetic acid (92 μl, 16.1 mmol) in THF (10 ml) is added a solution of tetra-n-butyl ammonium fluoride (1.63 ml, 1.0 Molar). After stirring at room temperature for 1 hour, the mixture is concentrated and co-evaporated with chloroform (50 ml). Purification by flash silica column chromatography (eluant chloroform:ethanol 9:1) gives Compound F isolated as a mixture of two diastereoisomers.

Found: C, 45.55; H, 6.85; N, 6.4% C$_{16}$H$_{27}$N$_2$O$_7$P.1 2/3H$_2$O requires C, 45.7; H, 7.25; N, 6.6% $^{31}$P nmr $^1$H decoupled (CDCl$_3$, 162 MHz) δ56.7, 56.5 ppm.

Compound G

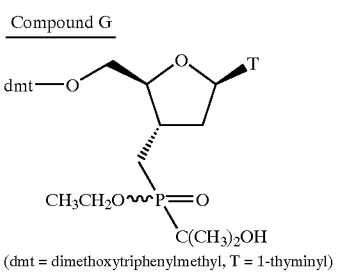

(dmt = dimethoxytriphenylmethyl, T = 1-thyminyl)

To a solution of Compound F (550 mg, 1.41 mmol) in pyridine (10 ml) is added dimethoxytritychloride (958 mg, 2.83 mmol). After stirring at room temperature for 20 hours, concentration and purification by flash silica column chromatography (eluant chloroform, methanol, triethylamine 100:5:1) gives Compound G, isolated as a mixture of 2 diastereoisomers.

$^{31}$P nmr $^1$decoupled (CDCl$_3$, 162 MHz) δ54.9, 54.7 ppm.

Compound H

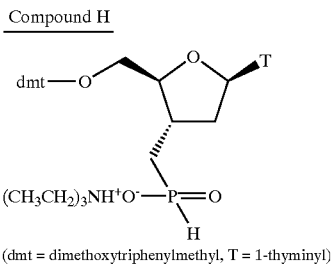

(dmt = dimethoxytriphenylmethyl, T = 1-thyminyl)

To a solution of Compound G (0.85 g, 1.22 mmol) in anhydrous methanol (10 ml) is added sodium methoxide (1.5 ml 4.4N solution in methanol). After stirring for 16 hours at room temperature, concentration and purification by flash silica column chromatography (gradient elution—chloroform, methanol, triethylamine 100:20:1–100:35:1), followed by further purification by passing a solution of the product in aqueous 0.5% triethylamine through a Dowex 50W-X2 ion exchange column (triethylamine form) gives, after concentration, Compound H.

$^{31}$P nmr $^1$H decoupled (CD$_3$OD, 162 MHz) δ23.7 ppm.

Compound J

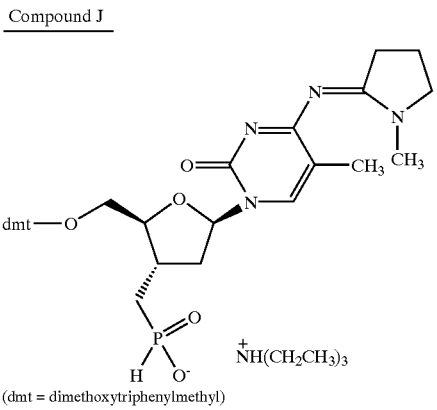

(dmt = dimethoxytriphenylmethyl)

Compound J is prepared as described in Example 98 of WO 96/08503.

In the formulae of Compounds K to M, T is 1-thyminyl, and DMTr is dimethoxytrityl.

Compound K

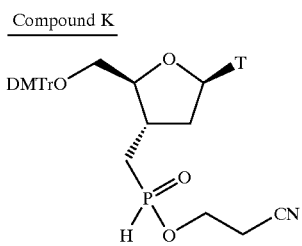

To a solution of Compound H (500 mg, 0.71 mmol) and dicyclohexylcarbodiimide (189 mg, 0.92 mmol) in dry THF (5.4 ml) under argon at room temperature is added 3-hydroxy propionitrile (58 μl, 0.85 mmol). The resulting solution is heated at 55° C. for 2 hours. After cooling, the mixture is filtered and diluted with ethyl acetate (20 ml) and washed with water and brine, dried over Na$_2$SO$_4$, filtered and concentrated. The resulting product is taken up in dichloromethane (5 ml) and filtered and concentrated, this process being repeated as required to remove dicyclohexyl urea, to give Compound K, isolated as a mixture of diastereoisomers at phosphorus.

$^{31}$P nmr ($^1$H decoupled) (CDCl$_3$, 162 MHz) δ37.4, 37.3 ppm.

Compounds L and M

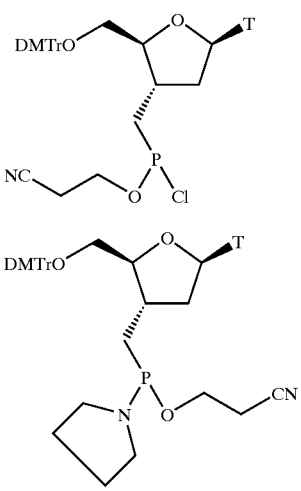

Compound L

Compound M

To a solution of carefully dried Compound K (71 mg, 220 μmol) in deuterochloroform (0.5 ml) containing pyridine (80 μl, 1 mmol) is added dichlorotriphenylphosphorane (113 mg, 350 μmol). The resulting mixture is shaken to dissolve the phosphorane and then allowed to stand at ambient temperature. The progress of the reaction is monitored by $^{31}$P nmr. The product is Compound L. After 16 hours, additional dichlorotriphenylphosphorane (28 mg, 87 μmol) is added. After an additional 24 hours, $^{31}$P nmr shows the reaction to be 95% complete. A total 56 μl (0.67 mmol) of pyrrolidine is added in portions to the crude reaction mixture at −30° C. The resulting mixture is allowed to warm to room temperature and then diluted with dichloromethane (20 ml), washed twice with deionised water (2×10 ml), dried (Na$_2$SO$_4$) and concentrated. Purification by flash silica column chromatography gives Compound M.

EXAMPLES 1–13

In the following Examples, Compound H and Compound J are utilised as monomers in the synthesis of oligonucleotide analogues. Unmodified 5′-dimethoxytrityl substituted nucleoside H-phosphonates are also utilised as the commercially available triethylammonium salts and abbreviated as follows:

Tp=Thymidine H-phosphonate
Cp=N$^4$-Benzoyl-deoxycytidine-H-phosphonate
Ap=N$^6$-Benzoyl-deoxyadenosine-H-phosphonate
Gp=N$^2$-Isobutyryl-deoxyguanosine-H-phosphonate.

The oligonucleotide syntheses are carried out manually in polypropylene syringes with commercially available nucleoside (Tp, Cp, or Ap) derivatised long chain alkylamine controlled pore glass. The first residue shown at the 3′ end of the following Examples results from this commercial material. The syntheses are carried out on a 0.2 μmol scale in the 3′ to 5′ direction.

Example 1

Oligonucleotide Analogue 1

5'TTT T*TC TCT CTC TCT3' SEQ ID NO:3
where * is an internucleoside linkage of formula I, where X is an oxygen and $R^1$ is hydroxy, all other linkages being phosphodiester linkages.

The support (6.8 mg) is washed with dichloromethane and the 5'-protecting group is removed by treatment with dichloroacetic acid and the support is washed again in preparation for coupling. Where the coupling is to be with an un-modified nucleoside H-phosphonate, the support is treated with a solution of the 5'-protected nucleoside H-phosphonate (30 mM for thymidine; 20 mM for cytidine) in pyridine-acetonitrile (1:1 v/v; 200 µl for thymidine, 300 µl for cytidine) in the presence of pivaloyl chloride (182 mM) also in pyridine-acetonitrile (1:1 v/v; 200 µl) for 1 minute.

To obtain the required oligonucleotide analogue normal H-phosphonate DNA synthesis is followed except that monomer Compound H is substituted for an unmodified nucleoside H-phosphonate when the T* position is reached in the synthesis and modified coupling and oxidation conditions are used as described below.

When the monomer is a 3'-methylene phosphinate of formula II, then the support is treated twice with a solution of Compound H (60 mM) in pyridine-acetonitrile (1:1 v/v; 200 µl) in the presence of pivaloyl chloride (121 mM) in pyridine-acetonitrile (1:1 v/v; 200 µl) for 30 minutes per treatment, that is to say 2×30 minutes. Additional wash steps are carried out and the cycle is repeated with the removal of the 5'-protecting group and the coupling of a fresh monomer, either Compound H or a 3'-H-phosphonate, to the free 5'-hydroxyl group of the growing oligonucleotide chain.

These steps are repeated until the full length 15-mer precursor to Oligonucleotide Analogue I has been prepared.

The steps of the synthetic cycle can be summarised as indicated below:

| Step | Reagent/Solvent | Volume |
| --- | --- | --- |
| 1-wash | dichloromethane | 4 ml |
| 2-deblock | 2.5% (v/v) dichloroacetic acid in dichloromethane | 4–5 ml |
| 3-wash | dichloromethane | 4 ml |
| 4-wash | pyridine-acetonitrile (1:1 v/v) | 4 ml |
| 5-coupling | i) Solution of Compound H (60 mM) in pyridine-acetonitrile (1:1 v/v) (200 µl) treated with pivaloyl chloride (121 mM) in pyridine-acetonitrile (1:1 v/v; 200 µl) and allowed to react for 2 × 30 minutes. | 400 µl |
|  | ii) monomers that are un-modified nucleoside H-phosphonates. The monomer solution (30 mM for Tp; 20 mM for Cp) in pyridine-acetonitrile (1:1 v/v; 200 µl for Tp, 200 µl + 100 µl pyridine for Cp) is treated with pivaloyl chloride (182 mM) in pyridine-acetonitrile (1:1 v/v; 200 µl) and allowed to react for 1 minute. | 400 µl (T) 500 µl (C) |
| 6-wash | pyridine-acetonitrile (1:1 v/v) | 4 ml |

7. Steps 1–6 are repeated with the appropriate monomers until the oligonucleotide precursor of Oligonucleotide Analogue I has been completed. After the final cycle of monomer addition has been carried out, the support-mounted oligomer is treated with iodine (0.2M) in pyridine-water (8:2 v/v) during 1 hour at ambient temperature, optionally followed by further treatment with iodine (0.2M), pyridine-triethylamine-water (6:1:1 v/v) during 1 hour at ambient temperature. This oxidises the internucleoside linkages. The support is then washed with pyridine-acetonitrile (1:1 v/v), to remove traces of iodine, followed by diethyl ether. The support is then air dried and transferred to a plastic tube for treatment with aqueous ammonia solution (30%) at 55° C. overnight. This removes the oligonucleotide analogue from the support and cleaves the base protecting groups whilst leaving the 5'-0-dimethoxytrityl group intact. After this treatment the oligonucleotide analogue solution is subject to 5'-0-dimethoxytrityl removal on an oligonucleotide purification cartridge according to standard procedures (Evaluating and Isolating Synthetic Oligonucleotides, Applied Biosystems, 1992). The oligonucleotide analogue is then purified by polyacylamide gel electrophoresis according to standard procedures.

MALDI-TOF mass spectroscopic analysis of Oligonucleotide Analogue I:

Calculated mass: 4424.3 Da
Found: 4423.8 Da

Example 2

Oligonucleotide Analogue 2

5'TTT T*TC TCT CTC TCT3' (SEQ ID NO:3)
where * is an internucleoside linkage of formula I where X is sulphur and $R^1$ is hydroxy. All other internucleoside linkages are phosphorothioate. The solid phase synthesis of the above oligonucleotide is carried out using the method of Example 1 above as far as the final cycle of monomer addition. The treatment of the oligomer with iodine used in Example 1 is replaced by a sulphurisation reaction. Thus, after the final coupling step, the support mounted precursor to Oligonucleotide Analogue 2 is treated with a solution of sulphur (5% w/v) in carbon disulphide-pyridine-triethylamine (10:10:1 v/v;2 ml) for 1–18 hours at room temperature, following the procedure of A. Audrus and G. Zon, *Nucleic Acids Research Symposium Series No. 20*, 1988, 121. At the completion of the incubation period, the support is washed with pyridine-acetonitrile (1:1 v/v) and diethylether then air-dried. The oligonucleotide analogue is removed from the support and protecting groups removed as described in Example 1.

MALDI-TOF (negative mode) mass spectroscopic analysis of Oligonucleotide Analogue 2:

Calculated mass: 4649.3 Da
Found: 4642.8 Da

Example 3

Oligonucleotide Analogue 3

5'TTT T*T$^{Me}$CTCT CTC TCT3' SEQ ID NO:4
where * is an internucleoside linkage of formula I, where X is oxygen and $R^1$ is hydroxy. All other internucleoside linkages are phosphodiester. $T^{me}$ is a thymidine residue having an α-methoxy group present at the 2'-position rather than a hydrogen atom. Solid phase synthesis of the above oligonucleotide is carried out, as described in Example 1, as far as nucleoside residue 11. Here, the support mounted precursor to oligonucleotide analogue 3 is treated with a solution of 5'-dimethoxytrityl-2'-O-methyl thymidine H-phosphonate (30 mM) in pyridine-acetonitrile (1:1 v/v; 200 µl) in the presence of pivaloyl chloride (182 mM) also in pyridine-acetonitrile (1:1 v/v; 200 µl) for 1 minute. The remainder of the synthesis is carried out as described in Example 1.

MALDI-TOF (negative mode) mass spectroscopic analysis of Oligonucleotide Analogue 3:
  Calculated mass: 4454.4 Da
  Found : 4448.6 Da Example 4

Oligonucleotide Analogue 4

5'TTT T*T$^{Me}$C TCT CTC TCT3' (SEQ ID NO: 4)
where * is an internucleoside linkage of formula I, where X is sulphur and R$^1$ is hydroxy. All other internucleoside linkages are phosphorothioate. T$^{Me}$ is a thymidine residue having an α-methoxy group present at the 2'-position rather than a hydrogen atom. The solid phase synthesis is carried out as described in Example 3 and the sulphurisation and subsequent work-up and deblocking are carried out as described in Example 2 above.

MALDI-TOF (negative mode) mass spectroscopic analysis of Oligonucleotide Analogue 4:
  Calculated mass: 4679.3 Da
  Found: 4664.1 Da Example 5

Oligonucleotide Analogue 5

5'TTT* TT3'
where * is an internucleoside linkage of formula I where X is oxygen and R$^1$ is hydroxy. All other internucleoside linkages are phosphodiester linkages.

This is prepared using the procedure of Example 1, except that Compound H and Compound Tp are the only nucleoside monomers used.

MALDI-TOF Mass Spectroscopic Analysis:
  Calculated Mass: 1457.1 Da
  Found: 1457.7 Da Example 6

Oligonucleotide Analogue 6

5'TTT TT*C TCT CTC TCT3' SEQ ID NO:5
where * is an internucleoside linkage of formula I where X is oxygen and R$^1$ is hydroxy. All other internucleoside linkages are phosphodiester linkages.

This is prepared using the general procedure of Example 1.

Example 7

Oligonucleotide Analogue 7

5'T*T*T* T*T*C TCT CTC TCT3' SEQ ID NO:6
Where * is an internucleoside linkage of formula I where X is oxygen and R$^1$ is hydroxy. All other linkages are phosphodiester linkages.

This is prepared using the general procedure of Example 1, but introducing five nucleoside residues from Compound H.

Example 8

Oligonucleotide Analogue 8

5'CGA CTA TGC AT*T T*TC3' SEQ ID NO:7
Where * is an internucleoside linkage of formula I where X is oxygen and R$^1$ is hydroxy. All other linkages are phosphodiester linkages.

This is prepared using the general procedure of Example 1, but introducing two nucleoside residues from Compound H. When the sequence requires the use of an A or G nucleoside then the coupling step of the method of Example 1 is modified as follows:
  i) 30 mM Ap or 30 mM Gp in pyridine-acetonitrile (1:1 v/v; 200 μl of Ap or Gp) is treated with pivaloyl chloride (182 mM) in pyridine-acetonitrile (1:1 v/v; 200 μl) and allowed to react for 1 minute.

MALDI-TOF mass spectroscopic analysis of Oligonucleotide Analogue 8:
  Calculated mass: 4514.1 Da
  Found: 4517.3 Da Example 9

Oligonucleotide Analogue 9

5'GCG T*T*T* T*T*T* T*T*T* T*GC G3' SEQ ID NO:8
Where * is an internucleoside linkage of formula I where X is oxygen and R$^1$ is hydroxy. All other linkages are phosphodiester linkages.

This is prepared using the general procedures of Examples 1 and 8, but introducing ten nucleoside residues from Compound H.

Example 10

Oligonucleotide Analogue 10

5'TTT TT*C* TCT CTC TCT3' SEQ ID NO:9
Where * is an internucleoside linkage of formula I where X is oxygen and R$^1$ is hydroxy. All other linkages are phosphodiester linkages.

This is prepared using the general procedure of Example 1, except that when the C* residue is to be introduced monomer Compound J is used as a direct replacement for Compound H.

Example 11

Oligonucleotide Analogue 11

5'TTT TTT TTT TTT TTT T*T*T* T3' SEQ ID NO:10
Where * is an internucleoside linkage of formula I where X is oxygen and R$^1$ is hydroxy. All other linkages are phosphodiester linkages.

This is prepared using the general procedure of Example 1, but introducing three nucleoside residues from Compound H.

Example 12

Oligonucleotide Analogue 12

5'T*T*C* T*C*G CCC GCT CC*T* C*C*T* C*C3' SEQ ID NO :11
Where is an internucleoside linkage of formula I where X is sulphur and R$^1$ is hydroxy. All other linkages are phosphorothioate.

This is prepared using the general procedure of Example 2. G residues are introduced as described in Example 8, and C* residues are introduced as described in Example 10.

Example 13

Oligonucleotide Analogue 13

5'T*T*C* T*C*G CTG GTG AGT* T*T*C* A3' SEQ ID NO:12
Where * is an internucleoside linkage of formula I where X is sulphur and R$^1$ is hydroxy. All other linkages are phosphorothioate.

This is prepared using the general procedure of Example 12. A residues are introduced as described in Example 8.

Example 14

Oligonucleotide Analogue 1 having the sequence 5'TTT tTC TCT CTC TCT3' (SEQ ID NO:13) where t represents a nucleoside unit derived from Compound M, is prepared by solid phase phosphoramidite oligonucleotide synthesis as described in 'Oligonucleotides and Analogues A practical Approach' ed F. Eckstein, IRL press 1991, except that Compound M is used instead of the usual 3'-phosphoramidite-substituted nucleoside at the appropriate point in the synthesis, so that an oligonucleotide precursor having an internucleoside linkage of formula XIV where $R^1_a$ is —$OCH_2CH_2CN$ is formed and then oxidised to an oligonucleotide having an internucleoside linkage of formula XV where $R^1_a$ is —$OCH_2CH_2CN$ and X is oxygen in the standard oxidation step, this oligonucleotide being coupled further to give Oligonucleotide Analogue 1.

---

What is claimed is:

1. An oligonucleotide analogue having 10 to 200 natural and/or synthetic nucleoside units linked by internucleoside linkages, and a 3'-terminal hydroxyl group, wherein at least one of the internucleoside linkages is of formula

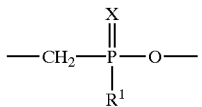

where
the indicated methylene group is attached to a 3' carbon atom of a nucleoside,
the indicated oxygen atom is attached to a 5'-carbon atom of an adjacent nucleoside,
$R^1$ is hydrogen, a group of formula $R^1_a$, or $-NR^1_b R^1_c$
wherein
$R^1_a$ is a $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group or a $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group bearing one or more terminal substituents; and
$R^1_b$ and $R^1_c$ are each independently an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group; and
x is oxygen or sulfur.

2. An oligonucleotide analogue according to claim 1, which has 15 to 40 nucleoside units.

3. An oligonucleotide analogue according to claim 1, which has 15 to 25 nucleoside units.

4. An oligonucleotide analogue according to claim 1 in which all the internucleoside linkages are of formula I.

5. An oligonucleotide analogue according to claim 1 in which up to 75% of the internucleoside linkages are of formula I.

6. An oligonucleotide analogue according to claim 5, in which up to 50% of the internucleoside linkages are of formula I.

7. An oligonucleotide analogue according to claim 6, in which up to 25% of the internucleoside linkages are of formula I.

8. An oligonucleotide analogue of claim 1, wherein at least two consecutive internucleoside linkages are of formula I.

9. An oligonucleotide analogue of claim 1, in which internucleoside linkages of formula I alternate with other internucleoside linkages.

10. An oligonucleotide analogue of claim 1, wherein the remaining internucleoside linkages are phosphodiester, phosphorothioate or phosphorodithioate linkages or a mixture of two or more thereof.

11. An oligonucleotide analogue according to claim 10, in which the remaining internucleoside linkages are phosphorothioate linkages.

12. An oligonucleotide analogue according to claim 10, further comprising a region having phosphodiester and/or phosphorothioate and/or phosphorodithioate internucleoside linkages between two regions having internucleoside linkages of formula I or a mixture thereof with phosphorothioate or phosphodiester linkages.

13. An oligonucleotide analogue according to claim 1, in which at least one nucleoside is modified at the 2' position thereof.

14. An oligonucleotide analogue according to claim 13, in which at least one nucleoside has a halogen atom or a group of formula $-OR^2$ at the 2' position, where $R^2$ is a $C_1$ to $C_{10}$ aliphatic group.

15. An oligonucleotide analogue according to claim 14, in which at least one nucleoside has a group $-OR^2$ at the 2' position, where $R^2$ is an unsubstituted or substituted $C_1$ to $C_{10}$ alkyl group.

16. An oligonucleotide analogue according to claim 15, in which $R^2$ is $C_1$ to $C_4$ alkyl, $C_1$ to $C_4$ alkoxy-substituted $C_1$ to $C_4$ alkyl or a group of formula $-(CH_2CH_2O)-_n R^3$ where $R^3$ is methyl or ethyl and n is 2 to 4.

17. An oligonucleotide analogue according to claim 16, in which $R^2$ is methyl, ethyl, methoxyethyl, ethoxyethyl or a group of formula $-(CH_2CH_2O)-_3 CH_3$.

18. An oligonucleotide analogue according to claim 13, in which at least two consecutive nucleosides are modified at the 2' position and are linked by phosphodiester internucleoside linkages and/or there is a linkage of formula I between a nucleoside unmodified at the 2' position and a 5' carbon atom of a nucleoside modified at the 2' position.

19. An oligonucleotide according to claim 1, in which $R^1_a$, $R^1_b$ or $R^1_c$ as alkyl, alkenyl, cycloalkyl, aryl, or aralkyl are unsubstituted or substituted by hydroxy, $C_1$ to $C_4$ alkoxy, halogen, cyano, tri($C_1$–$C_{15}$ hydrocarbyl)silyl or primary, secondary or tertiary amino.

20. An oligonucleotide analogue according to claim 1 in which $R^1$ is hydrogen, hydroxy, $O^-$, SH, $S^-$, an unsubstituted or substituted $C_1$ to $C_4$ alkyl or phenyl group, a group of formula $-OR^1_a$, where $R^1_a$ is an unsubstituted or substituted $C_1$ to $C_4$ alkyl, $C_3$ to $C_5$ alkenyl, $C_5$ to $C_8$ cycloalkyl or $C_7$ to $C_9$ aralkyl group, or a group of formula $-SR^1_a$ where $R^1_a$ is an unsubstituted or substituted $C_1$ to $C_4$ alkyl or phenyl group.

21. An oligonucleotide analogue according to claim 20, in which $R^1$ is hydrogen, hydroxy, $O^-$, SH, $S^-$, methoxy, ethoxy or 2-cyanoethoxy.

22. An oligonucleotide analogue according to claim 1 which is complementary to a region of mRNA for human c-raf kinase.

23. An oligonucleotide analogue according to claim 22 in which the nucleoside sequence is
5'-TCC CGC CTG TGA CAT GCA TT-3' (SEQ ID NO:1).

24. An oligonucleotide analogue according to claim 1, which is complementary to a region of mRNA for human PKC-α.

25. An oligonucleotide analogue according to claim 24, in which the nucleoside sequence is
5'-GTT CTC GCT GGT GAG TTT CA-3' (SEQ ID NO:2).

26. A method of preparing an oligonucleotide analogue having at least one internucleoside linkage of formula I

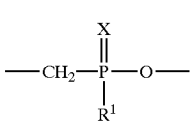

where $R^1$ and X are as defined in claim 1, which comprises (i) carrying out a coupling reaction or successive coupling reactions between (A) a natural or synthetic nucleoside or oligonucleotide having a 5'-hydroxyl group and (B) a natural or synthetic nucleoside or dinucleotide having at the 3'-position thereof a group reactive with said 5'-hydroxyl group until an oligonucleotide having the desired number of nucleosides is obtained, in at least one of said coupling reactions (B) being a nucleoside of formula

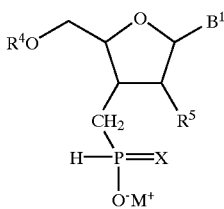

II where $B^1$ is a nucleoside base radical, $R^4$ is a hydroxy-protecting group, $R^5$ is hydrogen, hydroxy or a 2' modifying atom or group, $M^+$ is a metal or unsubstituted or substituted ammonium ion or a cation of a heterocyclic base, and X is oxygen or sulphur, and being reacted with (A) in the presence of a sterically hindered organic acid halide or anhydride to form an oligonucleotide analogue having a phosphinate internucleoside linkage of formula

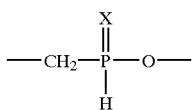

IA where X is oxygen or sulphur, and (ii)(a) oxidising the phosphinate linkage or (b) sulphurising the phosphinate linkage, or (c) reacting the phosphinate linkage with a compound of formula $R^1{}_aY$ where $R^1{}_a$ is as defined in claim 1 and Y is a leaving atom or group or (d) oxidising and reacting the phosphinate linkage with an alcohol of formula $R^1{}_aOH$ or an amine of formula $R^1{}_bNH_2$ or $R^1{}_bR^1{}_cNH$ where $R^1{}_a$, $R^1{}_b$ and $R^1{}_c$ are as defined in claim 1, or (e) silylating the phosphinate linkage and reacting the silylated linkage with a thioalkylating or thioarylating agent to give a phosphinate linkage of formula I where $R^1$ is —$SR^1{}_a$ where $R^1{}_a$ is as defined in claim 1.

27. A method according to claim 26, in which the oligonucleotide analogue is further reacted to replace the protecting group $R^4$ by hydrogen or, where $R^4$ is on a terminal nucleoside in the oligonucleotide analogue, by a 5' modifying group.

28. A method according to claim 26 which comprises the step of: carrying out the successive coupling reactions (i) and step (ii) of claim 26 with the nucleoside or oligonucleotide (A) attached to the solid support; (iii) detaching the oligonucleotide from the solid support and removing protecting groups to give an oligonucleotide having a terminal 5' free hydroxyl group; and (iv) optionally reacting the 5' free hydroxyl group to introduce a modifying group at the terminal 5' position.

29. A method according to claim 26 wherein, in formula II, $B^1$ is a pyrimidine base, $R^4$ is a methoxytrityl, dimethoxytrityl or tris tert-butyltrityl group, $R^5$ is hydrogen and $M^+$ is an unsubstituted ammonium, mono-, di- or tri-$C_1$–$C_{10}$ alkyl- or hydroxyalkyl-ammonium ion or a cation of a heterocyclic base.

30. A method according to claim 26 wherein the nucleoside of formula II is a stereoisomer having the formula:

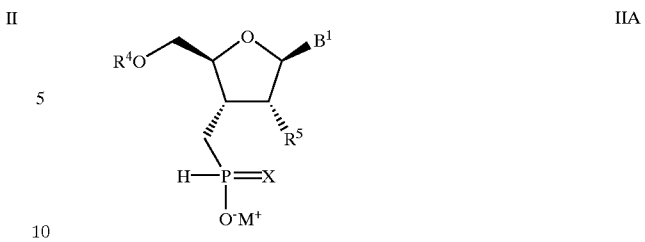

IIA

31. A method according to claim 26 wherein the coupling reaction of the nucleoside of formula II with (A) in the presence of a sterically hindered organic acid halide is carried out in the presence of a heterocyclic base having a tertiary nitrogen atom in the ring or an oxide thereof.

32. A method according to claim 26 wherein oxidation (ii)(a) is effected by treatment with iodine and water, or with tert-butyl hydroperoxide.

33. A method according to claim 26 wherein sulphurisation (ii)(b) is effected by treatment with sulphur in the presence of a tertiary amine in an organic solvent.

34. A method according to claim 26 wherein the reaction (ii)(c) of the phosphinate internucleoside linkage of formula 1A with a compound of formula $R^1{}_aY$ where $R^1{}_a$ is alkyl, cycloalkyl or aralkyl as defined in claim 1 and Y is halogen is carried out in the presence of a strong base.

35. A method according to claim 26 wherein the reaction (ii)(c) of the linkage of formula IA with a compound of formula $R^1{}_aY$, where $R^1{}_aY$ an alkenyl or aryl halide or triflate, is carried out in the presence of a palladium catalyst.

36. A method according to claim 26 wherein the oxidative reaction (ii)(d) of the phosphinate internucleoside linkage of formula IA with an alcohol of formula $R^1{}_aOH$ is carried out by reaction with an oxidant in the presence of the alcohol $R^1{}_aOH$ and a base.

37. A method according to claim 36, in which the oxidant is iodine, carbon tetrachloride or bromotrichloromethane, and the base is pyridine.

38. A method according to claim 26 wherein the oxidative reaction (ii)(d) of the phosphinate internucleoside linkage of formula IA is effected with an amine of formula $R^1{}_bNH_2$ or $R^1{}_bR^1{}_cNH$ where $R^1{}_b$ and $R^1{}_c$ are as defined in claim 1 and carbon tetrachloride or bromotrichloromethane or iodine to give an oligonucleotide analogue of the invention in which $R^1$ is —$NHR^1{}_b$ or —$NR^1{}_bR^1{}_c$ respectively.

39. A method according to claim 26 wherein the reaction (ii)(e) of the phosphinate linkage of formula IA is carried out by silylating the linkage using a trialkylsilyl halide and a base, and reacting the silylated linkage with a thioalkylating or thioarylating agent.

40. A method according to claim 39, in which the thioalkylating or thioarylating agent is a thiosulphonate of formula $ArSO_2SR^1{}_a$ where $R^1{}_a$ is as defined in claim 1 and Ar is an aromatic group.

41. A method according to claim 26 wherein when an oligonucleotide analogue having the desired number of nucleosides has been synthesised on a solid support, it is detached from the solid support, by treatment with concentrated aqueous ammonia, before or after treatment to remove hydroxy-protecting groups.

42. A method according to claim 26 wherein hydroxy-protecting groups are removed by treatment with an aqueous organic acid.

43. A method according to claim 26 wherein the nucleoside of formula II is replaced by a dinucleotide having the formula:

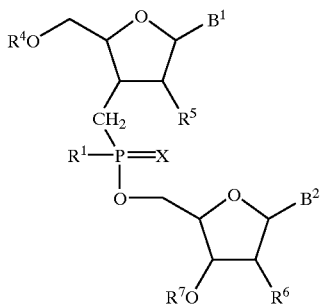

VIII

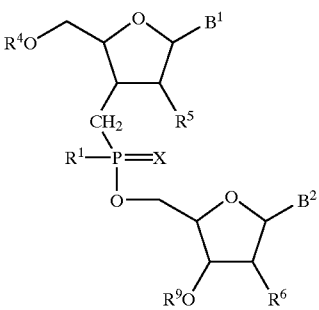

XI

45. A dinucleotide of formula where $B^1$ is a nucleoside base radical, $R^1$ is hydrogen, hydroxy, $O^-$, thiol, $S^-$, $-NH_2$ or a group of formula $R^1_a$, $-OR^1_a$, $-SR^1_a$, $-NHR^1_b$ or $-NR^1_b R^1_c$ where $R^1_a$ is an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group, $R^4$ is a hydroxy-protecting group and $R^5$ is hydrogen, hydroxy or a 2' modifying atom or group, $B^2$ is a nucleoside base radical, $R^6$ is hydrogen, hydroxy or a 2' modifying atom or group and $R^7$ is a group reactive with, or activatable to be reactive with, a 5' hydroxyl group in a nucleoside.

44. A method according to claim 43, in which $R^7O$ in formula VIII is a H-phosphonate group, a phosphoramidite group or a phosphodiester group.

where $B^1$ is a nucleoside base radical, $B^2$ is a nucleoside base radical, $R^1$ is hydrogen, hydroxy, $O^-$, thiol, $S^-$, $-NH_2$ or a group of formula $R^1_a$, $-OR^1_a$, $-SR^1_a$, $-NHR^1_b$ or $-NR^1_b R^1_c$ where $R^1_a$ is an unsubstituted or substituted $C_1$ to $C_{10}$ alkyl, $C_2$ to $C_{10}$ alkenyl, $C_3$ to $C_8$ cycloalkyl, $C_6$ to $C_{10}$ aryl or $C_7$ to $C_{13}$ aralkyl group, $R^4$ is a hydroxy-protecting group, $R^5$ is hydrogen, hydroxy or a 2' modifying atom or group, and $R^6$ is hydrogen, hydroxy or a 2' modifying atom or group except that where $R^1$ is other than hydrogen at least one of $R^5$ and $R^6$ is a 2' modifying atom or group and $R^9$ is a group reactive with, or activatable to be reactive with, a 5' hydroxyl group in a nucleoside or a hydroxy-protecting group.

* * * * *

UNITED STATES PATENT AND TRADEMARK OFFICE
CERTIFICATE OF CORRECTION

PATENT NO.     : 6,562,960 B1
DATED          : May 13, 2003
INVENTOR(S)    : Anthony David Baxter et al.

It is certified that error appears in the above-identified patent and that said Letters Patent is hereby corrected as shown below:

<u>Column 32,</u>
Line 14, please delete "-$(CH_2CH_2O)\text{-}_3CH_3$." and insert therefor -- -$(CH_2CH_2O)_3\text{-}CH_3$. --

Signed and Sealed this

Eighth Day of June, 2004

JON W. DUDAS
*Acting Director of the United States Patent and Trademark Office*